United States Patent
Okada

(10) Patent No.: US 9,303,274 B2
(45) Date of Patent: Apr. 5, 2016

(54) MICROORGANISM, AND HYDROGEN PRODUCTION PROCESS, 1,3-PROPANEDIOL PRODUCTION PROCESS AND BIODIESEL LIQUID WASTE TREATMENT METHOD EACH USING THE MICROORGANISM

(75) Inventor: Yukio Okada, Shibuya-ku (JP)

(73) Assignee: SAPPORO BREWERIES LIMITED, Tokyo (JP)

( * ) Notice: Subject to any disclaimer, the term of this patent is extended or adjusted under 35 U.S.C. 154(b) by 427 days.

(21) Appl. No.: 13/634,051

(22) PCT Filed: Mar. 30, 2011

(86) PCT No.: PCT/JP2011/058050
§ 371 (c)(1),
(2), (4) Date: Sep. 11, 2012

(87) PCT Pub. No.: WO2011/132511
PCT Pub. Date: Oct. 27, 2011

(65) Prior Publication Data
US 2013/0034889 A1    Feb. 7, 2013

(30) Foreign Application Priority Data

Apr. 19, 2010   (JP) ................................. 2010-096021

(51) Int. Cl.
*C12P 7/18* (2006.01)
*C12P 3/00* (2006.01)
*C12N 1/32* (2006.01)
*C12R 1/01* (2006.01)

(52) U.S. Cl.
CPC ... *C12P 7/18* (2013.01); *C12N 1/32* (2013.01); *C12P 3/00* (2013.01); *C12R 1/01* (2013.01); *Y02P 20/132* (2015.11)

(58) Field of Classification Search
None
See application file for complete search history.

(56) References Cited

U.S. PATENT DOCUMENTS 6,136,576 A * 10/2000 Diaz-Torres et al. ......... 435/158

FOREIGN PATENT DOCUMENTS

| JP | 2006 180782 | 7/2006 |
| JP | 2008-245600 A | 10/2008 |
| JP | 2009 183162 | 8/2009 |
| WO | WO 2008/052595 A1 | 5/2008 |
| WO | WO 2010/031793 A2 | 3/2010 |
| WO | WO 2010/031793 A3 | 3/2010 |

OTHER PUBLICATIONS

Selembo et al., Enhanced hydrogen and 1,3-Propanediol Production From Glycerol by Fermentation Using Mixed Cultures., Biotechnology and Bioengineering (Epub Jul. 21, 2009), vol. 104, pp. 1098-1106.*

Ito et al., Hydrogen and ethanol production from glycerol-containing wastes discharged after biodiesel manufacturing process., Journal of Bioscience and Bioengineering (2005), vol. 100, Issue 3, pp. 260-265.*

(Continued)

*Primary Examiner* — Alexander Kim
(74) *Attorney, Agent, or Firm* — Oblon, McClelland, Maier & Neustadt, L.L.P.

(57) ABSTRACT

The present invention provides a microorganism belonging to the genus *Enterobacter*, wherein the microorganism has an ability to assimilate glycerol to produce hydrogen gas and 1,3-propanediol, and wherein the microorganism is capable of assimilating glycerol in the presence of 10 mass % glycerol.

8 Claims, 7 Drawing Sheets

(56) References Cited

OTHER PUBLICATIONS

Matsusoe, R., et al., "Method for producing ethanol from glycerol-containing BDF waste fluid," Nippon Nogei Kagakukai Taikai Koen Yoshishu, vol. 2009, p. 336, 3P1359A, (2009) (with English translation).

Matsui, T., et al., "Effect of medium composition on H2 and ethanol fermentation from biodiesel castes by Enterovbacter aerogenes," Abstracts of the Annual Meeting of the Society for Biotechnology, vol. 58, 1D15-2, p. 64, (2006), (with English translation).

Ito, T., et al., "Hydrogen and Ethanol Production from Glycerol-Containing Wastes Discharged after Biodiesel Manufacturing Process," Journal of Bioscience and Bioengineering, vol. 100, No. 3, pp. 260-265, (2005).

Nakamura, K., et al., "Application of Waste Glycerin Liquid Produced from Bio-diesel Production to Methane Fermentation," Journal of the Japan Society Waste Management Experts, vol. 19, No. 1, pp. 9-16, (2008) (with English translation).

Mu, Y., et al., "Microbrial production of 1,3-propanediol by Klebsiella pneumoniae using crude glycerol from biosiesel preparations," Biotechnology Letters, vol. 28, No. 21, pp. 1755-1759, (2006).

International Search Report Issued Jun. 28, 2011 in PCT/JP11/58050 Filed Mar. 30, 2011.

Combined Office Action and Search Report issued Sep. 27, 2013 in Chinese Patent Application No. 201180019343.7 (with English Translation of Category of Cited Documents).

Anchana Pattanasupong, et al., "Production of 1,3-Propanediol from by-product of Biodiesel", Fourth Biomass Asia Workshop, Malasya, Nov. 20-22, 2007, 2 Pages (with English abstract).

Naresh Pachauri, et al., "Value-added Utilization of Crude Glycerol from Biodiesel Production: A Survey of Current Research Activities", an ASABE Meeting Presentation, Paper Number: 066223, Jul. 12, 2006, pp. 1-16.

International Preliminary Report on Patentability issued Nov. 15, 2012, in PCT/JP2011/058050 filed Mar. 30, 2011.

Written Opinion of the International Searching Authority issued Jun. 28, 2011, in PCT/JP2011/058050 filed Mar. 30, 2011.

Office Action issued Jan. 7, 2014 in Japanese Patent Application No. 2012-511597.

\* cited by examiner

MICROORGANISM, AND HYDROGEN PRODUCTION PROCESS, 1,3-PROPANEDIOL PRODUCTION PROCESS AND BIODIESEL LIQUID WASTE TREATMENT METHOD EACH USING THE MICROORGANISM

TECHNICAL FIELD

The present invention relates to a novel microorganism and a hydrogen production process, a 1,3-propanediol production process and a biodiesel liquid waste treatment method each using the microorganism.

BACKGROUND ART

Biodiesel refers to a fatty acid ester produced from fat and oil (triglyceride), such as vegetable oil and oil waste, used as a main raw-material and is expected to serve as alternative fuel for light oil, etc.

As a process for producing biodiesel, a chemical catalyst process has been widely used at present. In the chemical catalyst process, methanol and a catalyst (alkali) are added to a fat and oil to obtain a fatty acid methyl ester (FAME) as biodiesel through transesterification reaction. The reaction is expressed by the following chemical formula (1).

[Chemical Formula 1]

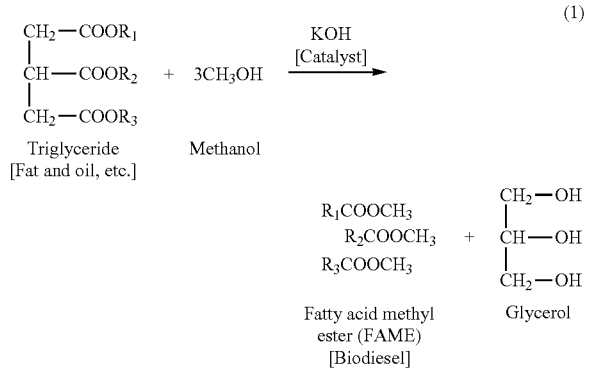

However, as shown in the above chemical formula (1), liquid waste (biodiesel liquid waste) containing glycerol in high concentration is produced as a by-product, and how to treat the liquid waste is a problem. An attempt to use biodiesel liquid waste as a raw material has been made to biologically produce energy and useful substances. This is called biorefinery.

For example, Patent Literatures 1 and 2 disclose bacteria belonging to *Enterobacter aerogenes* assimilating glycerol to produce hydrogen and ethanol, and a method of producing hydrogen and ethanol using the bacteria from glycerol contained in biodiesel liquid waste.

CITATION LIST

Patent Literature

Patent Literature 1: Japanese Patent Application Laid-Open No. 2009-183162

Patent Literature 2: Japanese Patent Application Laid-Open No. 2006-180782

SUMMARY OF INVENTION

Problems to be Solved by the Invention

Biodiesel liquid waste includes glycerol in extremely high concentration. However, bacteria belonging to *Enterobacter aerogenes* disclosed in Patent Literatures 1 and 2 have a problem: if the concentration of glycerol is high, an ability to assimilate glycerol is significantly inhibited, and thus, a sample containing glycerol in high concentration, such as biodiesel liquid waste, cannot be efficiently treated.

Then, the present invention is directed to providing a novel microorganism capable of assimilating glycerol even in the presence of high-concentration glycerol.

Means for Solving the Problems

The present invention provides a microorganism belonging to the genus *Enterobacter*, having an ability to assimilate glycerol to produce hydrogen gas and 1,3-propanediol, and capable of assimilating glycerol in the presence of 10 mass % glycerol.

The microorganism of the present invention has an ability to assimilate glycerol to produce hydrogen gas and 1,3-propanediol. Therefore, the microorganism can be used in biorefinery using glycerol as a raw material. Furthermore, the novel microorganism of the present invention can assimilate glycerol in the presence of high-concentration glycerol and thus enhance the efficiency of biorefinery.

The microorganism can preferably assimilate glycerol further even in the presence of 15 mass % glycerol. Furthermore, as the microorganism, *Enterobacter* sp. PEG8 strain, which was deposited at the Incorporated Administrative Agency National Institute of Technology and Evaluation Patent Microorganisms Depositary (NMPD) (2-5-8 Kazusakamatari, Kisarazu-shi, Chiba-ken 292-0818, Japan) under Accession No. NITE BP-901 on Feb. 12, 2010, may be used.

The microorganism can assimilate glycerol to produce hydrogen gas. The microorganism can also assimilate glycerol to produce 1,3-propanediol. Then, the present invention provides a hydrogen production process for producing hydrogen gas by the microorganism using glycerol as a substrate. The present invention also provides a 1,3-propanediol production process for producing 1,3-propanediol by the microorganism using glycerol as a substrate.

In the hydrogen production process and 1,3-propanediol production process, glycerol as mentioned above is preferably glycerol contained in biodiesel liquid waste. Since the microorganism can assimilate glycerol in the presence of high-concentration glycerol, biodiesel liquid waste containing glycerol in high concentration can be efficiently treated.

The present invention also provides a method for treating biodiesel liquid waste (biodiesel liquid waste treatment method), comprising a degradation step of degrading glycerol contained in biodiesel liquid waste by the microorganism.

It is preferable that the biodiesel liquid waste treatment method further comprises a recovery step of recovering hydrogen gas or 1,3-propanediol produced in the degradation step. Since the microorganism can degrade glycerol to produce hydrogen gas and 1,3-propanediol that can be used as energy or a useful substance, biorefinery can be efficiently performed by recovering these.

The present invention further provides a biodiesel liquid waste treatment method, comprising: bringing a raw-material liquid containing biodiesel liquid waste and the microorganism into contact with each other to degrade glycerol in the biodiesel liquid waste, and decreasing glycerol up to a pre-determined concentration, and then, exchanging at least part of the raw-material liquid with decreased glycerol with another raw-material liquid containing biodiesel liquid waste.

In the biodiesel liquid waste treatment method, it is preferable that glycerol in the biodiesel liquid waste is degraded to decrease glycerol up to a pre-determined concentration; at the same time, hydrogen gas or 1,3-propanediol produced is recovered and thereafter exchange is made with another raw-material liquid containing biodiesel liquid waste.

Effects of the Invention

According to the novel microorganism of the present invention, since glycerol can be assimilated even in the presence of high-concentration glycerol, biodiesel liquid waste, etc., containing glycerol in high concentration can be efficiently treated.

Furthermore, the novel microorganism of the present invention can assimilate glycerol to produce hydrogen gas, ethanol and 1,3-propanediol. Therefore, a wide variety of energy substances and useful substances can be produced and biorefinery using glycerol as a raw material can be efficiently performed.

EMBODIMENTS FOR CARRYING OUT THE INVENTION

Figure 1:
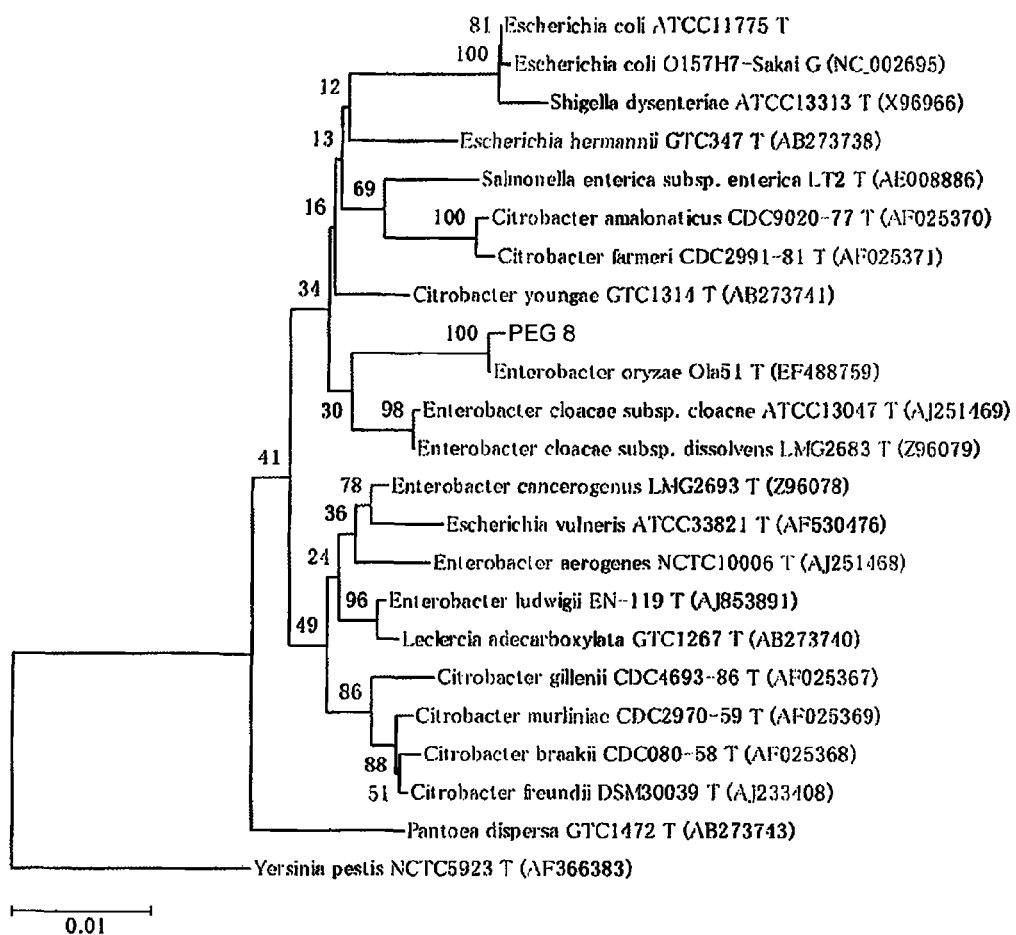
[FIG. 1] This figure shows the results of a simplified molecular phylogenetic analysis of 16S rDNA nucleotide sequence.

The microorganism of the present invention belongs to the genus *Enterobacter* and can assimilate glycerol to produce hydrogen gas and 1,3-propanediol and can assimilate glycerol, even in the presence of 10 mass % glycerol, to produce hydrogen gas.

It is preferable that the microorganism can assimilate glycerol further even in the presence of 15 mass % glycerol.

In the embodiment, the microorganism preferably exhibits bacteriological properties shown in Table 1.

TABLE 1

| Bacteriological properties | |
|---|---|
| Item | Property |
| Cell morphology | *Bacillus* |
| Presence or absence of spores | − |
| Gram staining | − |
| Mobility | + |
| Growth at 37° C. | + |
| Growth at 45° C. | + |
| Catalase reaction | + |
| Oxidase reaction | − |
| Acid/gas generation from glucose | +/+ |
| Oxidation/fermentation of glucose | +/+ |
| β-galactosidase activity | + |
| Arginine dihydrolase activity | + |
| Lysine decarboxylase activity | − |
| Ornithine decarboxylase activity | − |
| Urease activity | − |
| Citric acid availability | + |
| Acetoin production activity | + |
| Gelatinase activity | − |
| D-mannitol assimilation | + |
| D-sorbitol assimilation | + |
| L-rhamnose assimilation | + |
| Growth at 4° C. | − |
| Growth in KCN medium | + |

Note that "+" represents being positive and "−" represents being negative.

The microorganism preferably forms opaque yellow colonies having a diameter of 2.0-3.0 mm with the entire periphery fringe, being circular and having a smooth lenticular surface, when cultured on LB agar medium at 30° C. for 48 hours.

Furthermore, the microorganism preferably has a 16S rDNA nucleotide sequence having a homology of 99.7% or more with the nucleotide sequence identified by SEQ ID No. 1, more preferably has a 16S rDNA nucleotide sequence having a homology of 99.8% or more, and further preferably has 16S rDNA nucleotide sequence having a homology of 99.9% or more.

As the microorganism, *Enterobacter* sp. PEG8 strain, which was deposited at the Incorporated Administrative Agency National Institute of Technology and Evaluation Patent Microorganisms Depositary (NMPD) (2-5-8 Kazusakamatari, Kisarazu-shi, Chiba 292-0818, Japan) under Accession No. NITE BP-901 on Feb. 12, 2010, can be used.

The microorganism according to the present invention can be isolated by screening a sample (microorganisms) taken, for example, from discharged water from a biodiesel manufacturing plant based on the proliferation potential in the presence of glycerol, as an indicator. Furthermore, screening may be performed based on hydrogen gas production capacity or 1,3-propanediol production capacity in the presence of glycerol as an indicator, in addition to the proliferation potential in the presence of glycerol.

To describe the method more specifically, for example, a medium (for example, peptone: 2.5 g/L, yeast extract: 2.5 g/L, pH6.8) containing glycerol alone as a carbon source in a concentration of 1 to 20 mass % is placed in a culture flask and a small amount of sample taken from discharged water, etc., of a biodiesel manufacturing plant is further added as a microorganism source. This is cultured under appropriate conditions (for example, under an anaerobic condition, 37° C., 24 hours, while allowing the culture to stand still or stirring to the extent that the microorganism does not precipitate). In this manner, a microorganism capable of assimilating glycerol and further having glycerol tolerance can be preferentially proliferated.

Note that, the glycerol tolerance refers to the ability to survive or proliferate even in the presence of (high-concentration) glycerol. The ability to assimilate glycerol even in the presence of (high concentration) glycerol is an example of glycerol tolerance.

Furthermore, after culturing, if hydrogen gas contained in the culture flask is quantified, a sample producing hydrogen gas can also be selected. Hydrogen gas can be quantified, for example, by measuring the amount of gas collected in a gas collection bag connected to the culture flask and analyzing the composition of the collected gas by gas chromatography. Furthermore, after culturing, if 1,3-propanediol contained in the culture solution is quantified, a sample producing 1,3-propanediol can also be selected. Quantification of 1,3-propanediol can be made, for example, by liquid chromatography.

From the microorganisms proliferated by culturing, the microorganism according to the present invention can be isolated by pure separation. Pure separation can be carried out by a method well known to those skilled in the art. To describe more specifically, pure-separation colonies can be formed by inoculating microorganisms on agar medium and culturing them. A desired microorganism can be isolated by picking up a colony. It is preferable that glycerol has been added to the agar medium.

Furthermore, after culturing, an aliquot is taken from the culture solution, inoculated (again) in a fresh medium containing glycerol placed in a culture flask and cultured again. The cultured sample may be subjected to the aforementioned pure separation (pure culture) or this culture cycle can be also repeated. If the number of culture cycles is increased, a desired microorganism can be accumulated.

The microorganism isolated as mentioned above is subjected to identification and analysis for property, nature, and the like, which can be made by use of various identification test methods known in the art or commercially available identification kits. Alternatively, the microorganism can be also identified by sequencing a 16S rDNA nucleotide sequence and subjecting to homology search and molecular phylogenetic analysis.

The present invention includes, as an embodiment, a hydrogen production process for producing hydrogen gas by the microorganism using glycerol as a substrate.

In the hydrogen production process, the microorganism and a raw-material liquid containing glycerol serving as a substrate are brought into contact with each other to allow the microorganism to ferment the substrate to produce hydrogen. Examples of the hydrogen fermentation method include a liquid culturing method, in which the microorganism is cultured in a raw-material liquid after subjecting the microorganism to seed culture or without subjecting it to seed culture, and a method of inserting a support or carrier having the microorganism immobilized thereto in a raw-material liquid.

Furthermore, the culture method can be varied depending upon the method of supplying a raw-material liquid. To describe it more specifically, examples thereof include a method (perfusion culture method), in which culture is continuously performed by supplying a raw-material liquid at a constant rate, while removing the same amount of raw-material liquid; a method (batch culture method), in which a fresh raw-material liquid is prepared every single culture process and culture is performed without supply or removal of a raw-material liquid (component) during culturing; a method (repetitive batch culture), in which culture is made in the same manner as in a batch culture without supply or removal of a raw-material liquid (component) during culturing and a fresh raw-material liquid is supplied to part of the culture solution, and then, batch culture is repeated; and a method (feeding culture method), in which culture is basically performed in the same manner as in the batch culture except that only a specific component of a raw-material liquid is supplementally added during culturing. Of them, in the hydrogen production process of the embodiment, the repetitive batch culture is preferable in view of avoiding a reduction of hydrogen gas production efficiency due to by-products.

The raw-material liquid for use in hydrogen production is not particularly limited as long as it contains glycerol. Specific examples thereof include soap-production liquid waste and biodiesel liquid waste. Of them, biodiesel liquid waste is preferable. Since the biodiesel liquid waste contains a large amount of glycerol and, in addition, glycerol has no useful use, it can be preferably used as a raw material in this embodiment. Note that, the content of the biodiesel liquid waste contained in a raw-material liquid may be appropriately set in consideration of e.g., hydrogen production efficiency (cost, yield, etc.,), for example, between 0.1 and 35 mass % in terms of glycerol concentration.

Furthermore, the raw-material liquid may contain not only glycerol but also nutrient components (e.g., carbon source other than glycerol, nitrogen source), a growth promoter, a sterilizer such as an antibiotic, a pH regulator, a dispersant, an emulsifier, an antifoaming agent and the like.

As reaction conditions (culture conditions) for hydrogen fermentation, for example, reaction temperature (culture temperature) can be set between 10 and 45° C. and preferably between 15 and 40° C. Furthermore, pH can be set between 4.0 and 9.0 and preferably between 4.5 and 8.0. Furthermore, the reaction time can be set at, for example, 6 to 48 hours. Alternatively, glycerol concentration of a raw-material liquid is measured in real time and the reaction may be terminated when the measurement value of glycerol reached a pre-determined concentration or less. As a method of determining the glycerol concentration in a reaction solution, for example, a liquid chromatographic measurement method etc. can be mentioned. Furthermore, "the pre-determined concentration" may be appropriately set in consideration of e.g., hydrogen production efficiency (cost, yield, etc.). For example, the concentration may be set at 1.0 mass % or 0.5 mass %. Furthermore, the concentration may be set at 0 mass % (glycerol is completely degraded).

In the specification, biodiesel liquid waste refers to liquid waste containing glycerol resulting from a process in which fat and oil is converted into a methyl (or ethyl) ester compound and a fatty acid methyl (or ethyl) ester (biodiesel) is removed.

Examples of the fat and oil include, but not particularly limited to, vegetable oils such as rapeseed oil, palm oil, olive oil, sunflower oil, soybean oil, rice oil and hemp oil (hempseed oil); fish oil; animal fats such as lard and beef fat; and waste edible oil (so-called frying oil, etc.).

Furthermore, as another embodiment, a 1,3-propanediol production process for producing 1,3-propanediol by the microorganism using glycerol as a substrate is also included in the present invention.

In the 1,3-propanediol production process, the microorganism and a raw-material liquid containing glycerol serving as a substrate are brought into contact with each other to allow the microorganism to ferment it to produce 1,3-propanediol. Examples of the 1,3-propanediol fermentation method include a liquid culturing method in which the microorganism is cultured in a raw-material liquid after subjecting the microorganism to seed culture or without subjecting it to seed culture; and a method of inserting a support or carrier having the microorganism immobilized thereto in a raw-material liquid.

Furthermore, examples of a method for supplying a raw-material liquid include a perfusion culture method, a batch culture method, a repetitive batch culture and a feeding culture method. Of them, in the 1,3-propanediol production process in the embodiment, the repetitive batch culture is preferable in view of avoiding a reduction in 1,3-propanediol production efficiency due to by-products.

The raw-material liquid for use in 1,3-propanediol production is not particularly limited as long as it contains glycerol. Specific examples thereof include soap-production liquid waste and biodiesel liquid waste. Of them, biodiesel liquid waste is preferable. The content of biodiesel liquid waste contained in a raw-material liquid may be appropriately set in consideration of e.g., hydrogen production efficiency (cost, yield, etc.,), for example, between 0.1 and 35 mass % in terms of glycerol concentration.

Furthermore, the raw-material liquid may contain not only glycerol but also nutrient components (e.g., carbon source other than glycerol, nitrogen source), a growth promoter, a sterilizer such as an antibiotic, a pH regulator, a dispersant, an emulsifier, an antifoaming agent and the like.

As reaction conditions (culture conditions) for 1,3-propanediol fermentation, for example, reaction temperature (culture temperature) can be set between 10 and 45° C. and more preferably between 15 and 40° C. Furthermore, pH can be set between 4.0 and 9.0 and preferably between 4.5 and 8.0. Furthermore, the reaction time can be set at, for example, 6 to 48 hours. Alternatively, glycerol concentration of a raw-material liquid is measured in real time and the reaction may be terminated when the measurement value of glycerol reached a pre-determined concentration or less. As a method of determining the glycerol concentration in a reaction solution, for example, a liquid chromatographic measurement method etc. can be mentioned. Furthermore, "the pre-determined concentration" may be appropriately set in consideration of e.g., hydrogen production efficiency (cost, yield, etc.). For example, the concentration may be set at 1.0 mass % or 0.5 mass %. Furthermore, the concentration may be set at 0 mass % (glycerol is completely degraded).

Furthermore, the present invention include, as another embodiment, a method for treating biodiesel liquid waste including a degradation step of degrading glycerol contained in biodiesel liquid waste by the microorganism. In this embodiment, it is preferable that the method further has a step of recovering hydrogen gas or 1,3-propanediol produced with the progress of glycerol degradation.

In the method for treating biodiesel liquid waste, in the degradation step, the microorganism and glycerol-containing biodiesel liquid waste serving as a substrate are brought into contact with each other to assimilate glycerol by the microorganism. The biodiesel liquid waste is preferably diluted up to a predetermined glycerol concentration to prepare a raw-material liquid containing biodiesel liquid waste and then brought into contact with the microorganism. The predetermined glycerol concentration may be appropriately set in consideration of e.g., treatment efficiency (cost, etc.,) of biodiesel liquid waste, for example, between 0.1 and 35 mass %.

Examples of the method for assimilating glycerol include a method of culturing the microorganism in a raw-material liquid after subjecting the microorganism to seed culture or without subjecting it to seed culture; and a method of inserting a support or carrier having the microorganism immobilized thereto in a raw-material liquid. Furthermore, examples of a method for supplying a raw-material liquid include a perfusion culture method, a batch culture method, a repetitive batch culture and a feeding culture method. Of them, the repetitive batch culture is preferable as the treatment method in this embodiment, in view of suppressing an effect of by-products upon a reduction in treatment efficiency to a minimum.

Furthermore, the raw-material liquid may contain not only glycerol but also nutrient components (e.g., carbon source other than glycerol, nitrogen source), a growth promoter, a sterilizer such as an antibiotic, a pH regulator, a dispersant, an emulsifier, an antifoaming agent and the like.

As reaction conditions (culture conditions) for glycerol assimilation, for example, reaction temperature (culture temperature) can be set between 10 and 45° C. and preferably between 15 and 40° C. Furthermore, pH can be set between 4.0 and 9.0 and preferably between 4.5 and 8.0. Furthermore, the reaction time can be set at, for example, 6 to 48 hours. Alternatively, glycerol concentration of a raw-material liquid is measured in real time and the reaction may be terminated when the measurement value of glycerol reached a pre-determined concentration or less. As a method for determining the glycerol concentration in a reaction solution, for example, a liquid chromatographic measurement method etc. can be mentioned. Furthermore, "the pre-determined concentration" may be appropriately set in consideration of e.g., hydrogen production efficiency (cost, yield, etc.). For example, the concentration may be set at 1.0 mass % or 0.5 mass %. Furthermore, the concentration may be set at 0 mass % (glycerol is completely degraded).

It is preferable that the method for treating biodiesel liquid waste further has a recovery step of recovering hydrogen gas or 1,3-propanediol produced with the progress of degradation of glycerol. Hydrogen gas can be recovered by attaching a pipe for recovering hydrogen gas to a reaction vessel (culture vessel) and the recovery step is performed in parallel with the degradation step. Furthermore, 1,3-propanediol can be recovered by recovering a raw-material liquid after the degradation step and subjecting it to distillation or the like.

Furthermore, the present invention provides, as another embodiment, a method for treating biodiesel liquid waste in which a raw-material liquid containing biodiesel liquid waste and the microorganism are brought into contact with each other to degrade glycerol in the biodiesel liquid waste, thereby decreasing glycerol to a pre-determined concentration, and thereafter, at least part of the raw-material liquid with decreased glycerol content is exchanged with another raw-material liquid containing biodiesel liquid waste. In the method for treating biodiesel liquid waste, it is possible that glycerol is decreased up to the pre-determined concentration; at the same time, hydrogen gas or 1,3-propanediol produced is recovered and then exchanged with another raw-material liquid containing biodiesel liquid waste.

In this embodiment, the microorganism and a glycerol-containing biodiesel liquid waste serving as a substrate are brought into contact with each other to allow the microorganism to assimilate glycerol. It is preferable that the biodiesel liquid waste is diluted so as to satisfy a predetermined glycerol concentration to prepare a raw-material liquid containing biodiesel liquid waste and then brought into contact with the microorganism. The predetermined glycerol concentration may be appropriately set in consideration of e.g., treatment efficiency (cost, etc.,) of biodiesel liquid waste, for example, between 0.1 and 35 mass % in terms of glycerol concentration.

Examples of the assimilation method for glycerol include a method of culturing the microorganism in a raw-material liquid after subjecting the microorganism to seed culture or without subjecting it to seed culture; and a method of inserting a support or carrier having the microorganism immobilized thereto in a raw-material liquid. Furthermore, this embodiment is characterized in that batch culture is repeatedly performed (repetitive batch culture).

The raw-material liquid may contain not only glycerol but also nutrient components (e.g., carbon source other than glycerol, nitrogen source), a growth promoter, a sterilizer such as an antibiotic, a pH regulator, a dispersant, an emulsifier, an antifoaming agent and the like.

As reaction conditions (culture conditions) for glycerol assimilation, for example, reaction temperature (culture temperature) can be set between 10 and 45° C. and preferably between 15 and 40° C. Furthermore, pH can be set between 4.0 and 9.0 and preferably between 4.5 and 8.0. Furthermore, the reaction time can be set at, for example, 6 to 48 hours. Alternatively, glycerol concentration of a raw-material liquid is measured in real time and the reaction may be terminated when the measurement value of glycerol reached a pre-determined concentration or less. As a method for determining the glycerol concentration in a reaction solution, for example, a liquid chromatographic measurement method etc. can be mentioned. Furthermore, "the pre-determined concentration" may be appropriately set in consideration of e.g., hydrogen production efficiency (cost, yield, etc.). For example, the concentration may be set at 1.0 mass % or 0.5 mass %. Furthermore, the concentration may be set at 0 mass % (glycerol is completely degraded).

In this embodiment, it is preferable to recover hydrogen gas or 1,3-propanediol produced with the progress of degradation of glycerol. Hydrogen gas can be recovered by attaching a pipe for recovering hydrogen gas to a reaction vessel (culture vessel) and recovery can be made in parallel with degradation of glycerol. Furthermore, 1,3-propanediol can be recovered by recovering a raw-material liquid after the reaction (after culturing) and subjecting it to distillation or the like.

The repetitive batch culture method in this embodiment can be also said as a treatment method for biodiesel liquid waste, including a step of bringing a raw-material liquid containing biodiesel liquid waste and the microorganism into contact with each other, a step of degrading glycerol in biodiesel liquid waste by the microorganism to decrease glycerol up to a pre-determined concentration and a step of exchanging at least part of the raw-material liquid with decreased glycerol with another raw-material liquid containing biodiesel liquid waste. Furthermore, in the step of decreasing glycerol to a pre-determined concentration, hydrogen gas or 1,3-propanediol produced is preferably recovered.

EXAMPLES

Example 1

[Screening for Glycerol-assimilating Hydrogen-producing Bacteria]

A glycerol-assimilating hydrogen-producing bacteria were searched by enrichment culture using discharged water from a biodiesel (FAME) manufacturing plant as a microorganism source.

To FAME medium (composition: biodiesel liquid waste was added in a concentration of 1 mass % in terms of glycerol concentration, peptone: 2.5 g/L, yeast extract: 2.5 g/L, pH6.8), discharged water from a biodiesel manufacturing plant was added and the mixture was subjected to enrichment culture under an anaerobic condition, at 37° C. for 24 hours in a medium bottle equipped with a gas collection bag. The amount of biogas collected in the gas collection bag was measured and the composition of the gas was analyzed by gas chromatography (GC-14B manufactured by Shimadzu) to determine the amount of hydrogen gas. Conditions for gas composition analysis are as follows.

Detector: TCD (60 mA)
Column: PorapakN, molecular sieve 13×, PorapakQ
Carrier gas: Argon
Column temperature: 60° C.
Injection temperature: 60° C.
Detector temperature: 80° C.

After culturing, the culture solution (50 ml) was added to a fresh FAME medium (200 ml). In this manner, a subculture was performed and culturing was repeatedly performed until hydrogen gas was produced in a stable amount. After hydrogen gas was stably generated, the culture solution was seeded in glycerol agar medium (glycerol: 10 g/L, peptone: 2.5 g/L, yeast extract: 2.5 g/L, agar: 15 g/L, pH6.8) and cultured in an incubator at 37° C. for 48 hours under an anaerobic condition to form colonies. The colonies formed were isolated and seeded in a 20 ml vial containing FAME medium (10 ml) and cultured airtight under an anaerobic condition at 37° C. for 24 hours. After culturing, hydrogen gas contained in a vacant space of the vial was quantified by the aforementioned method to select a bacteria strain producing hydrogen gas.

Example 2

[Identification of PEG8 Strain by 16S rDNA Nucleotide Sequence Analysis]

PEG8 strain, which was one of the bacteria strains obtained in Example 1, was subjected to 16S rDNA nucleotide sequence analysis to identify the bacteria strain.

DNA was extracted from PEG8 strain by use of InstaGene Matrix (manufactured by BioRad) and amplified by PCR using PrimeSTAR HS DNA Polymerase (manufactured by Takara Bio Inc.) to obtain the whole length 16S rDNA. Using the obtained PCR product as a template, cycle sequence was performed by use of BigDye Terminator v3.1 Cycle Sequencing Kit (manufactured by Applied Biosystems). The sample obtained after cycle sequence was applied was subjected to nucleotide sequence data analysis performed by using ABI PRISM 3130×1 Genetic Analyzer System (manufactured by Applied Biosystems). The analyzed data was further analyzed by use of software of ChromasPro1.4 (Technelysium Pty Ltd.) to determine the nucleotide sequence (SEQ ID No. 1). Each experimental procedure was performed in accordance with the manual attached to each kit.

The determined 16S rDNA nucleotide sequence of the PEG8 strain was subjected to homology search using software, i.e., Apollon 2.0 (manufactured by TechnoSuruga Laboratory) for Apollon DB-BA ver 5.0 (manufactured by TechnoSuruga Laboratory) database or International nucleotide sequence database (GenBank/DDBJ/EMBL). As a result of the search for Apollon DB-BA ver 5.0 database, the 16S rDNA nucleotide sequence of PEG8 strain had a homology of 97.6% with the 16S rDNA nucleotide sequence of *Enterobacter cloacae* subsp. *cloacae* ATCC13047 strain (Table 2). Furthermore, as a result of search using International nucleotide sequence database, the 16S rDNA nucleotide sequence of PEG8 strain had a high homology with the 16S rDNA nucleotide sequence derived from the genus *Enterobacter* and had a homology of 99.6% with *Enterobacter oryzae* Ola50 strain (Table 3).

TABLE 2

Results of homology search using Apollon DB-BA ver. 5.0 database (the top 20)

| Registered name | Strain name | Accession No. | Homology |
|---|---|---|---|
| Enterobacter cloacae subsp. cloacae | ATCC13047 | AJ251469 | 1444/1479 (97.6%) |
| Enterobacter cloacae subsp. dissolvens | LMG2683 | Z96079 | 1444/1481 (97.5%) |
| Citrobacter amalonaticus | CDC9020-77 | AF025370 | 1455/1502 (96.9%) |
| Enterobacter cancerogenus | LMG2693 | Z96078 | 1439/1481 (97.2%) |
| Leclercia adecarboxylata | GTC1267 | AB273740 | 1444/1486 (97.2%) |
| Enterobacter ludwigii | EN-119 | AJ853891 | 1439/1481 (97.2%) |
| Citrobacter braakii | CDC080-58 | AF025368 | 1452/1502 (96.7%) |
| Citrobacter youngae | GTC1314 | AB273741 | 1446/1488 (97.2%) |
| Escherichia coli | ATCC11775 | — | 1449/1502 (96.5%) |
| Escherichia coli | O157H7-Sakai | NC_002695 | 1451/1502 (96.6%) |
| Shigella dysenteriae | ATCC13313 | X96966 | 1442/1487 (97.0%) |
| Citrobacter murliniae | CDC2970-59 | AF025369 | 1450/1502 (96.5%) |
| Citrobacter farmeri | CDC2991-81 | AF025371 | 1441/1486 (97.0%) |
| Escherichia vulneris | ATCC33821 | AF530476 | 1426/1468 (97.1%) |
| Escherichia hermannii | GTC347 | AB273738 | 1441/1488 (96.8%) |
| Enterobacter aerogenes | NCTC10006 | AJ251468 | 1432/1479 (96.8%) |
| Citrobacter gillenii | CDC4693-86 | AF025367 | 1446/1502 (96.3%) |
| Citrobacter freundii | DSM30039 | AJ233408 | 1440/1490 (96.6%) |
| Salmonella enterica subsp. enterica | LT2 | AE008886 | 1446/1502 (96.3%) |
| Pantoea disperse | GTC1472 | AB273743 | 1438/1487 (96.7%) |

TABLE 3

Results of homology search using International base sequence database (the top 20)

| Registered name | Strain name | Accession No. | Homology |
|---|---|---|---|
| Enterobacter oryzae | Ola50 | EF488758 | 1474/1480 (99.6%) |
| Enterobacter oryzae | Ola01 | EF488760 | 1473/1480 (99.5%) |
| Enterobacter oryzae | Ola51 | EF488759 | 1473/1480 (99.5%) |
| uncultured Enterobacter sp. | — | GQ417351 | 1458/1463 (99.7%) |
| uncultured Enterobacter sp. | — | GQ417309 | 1458/1463 (99.7%) |
| uncultured Enterobacter sp. | — | GQ417278 | 1458/1463 (99.7%) |
| uncultured Enterobacter sp. | — | GQ417628 | 1457/1463 (99.6%) |
| uncultured Enterobacter sp. | — | GQ417343 | 1457/1463 (99.6%) |
| uncultured Enterobacter sp. | — | GQ417342 | 1457/1463 (99.6%) |
| uncultured Enterobacter sp. | — | GQ417302 | 1457/1463 (99.6%) |
| uncultured Enterobacter sp. | — | GQ417285 | 1457/1463 (99.6%) |
| uncultured Enterobacter sp. | — | GQ417236 | 1457/1463 (99.6%) |
| uncultured Enterobacter sp. | — | GQ417353 | 1458/1464 (99.6%) |
| uncultured Enterobacter sp. | — | GQ417687 | 1456/1463 (99.5%) |
| uncultured Enterobacter sp. | — | GQ417553 | 1456/1463 (99.5%) |
| uncultured Enterobacter sp. | — | GQ417513 | 1456/1463 (99.5%) |
| uncultured Enterobacter sp. | — | GQ417510 | 1456/1463 (99.5%) |
| uncultured Enterobacter sp. | — | GQ417507 | 1456/1463 (99.5%) |
| uncultured Enterobacter sp. | — | GQ417498 | 1456/1463 (99.5%) |
| uncultured Enterobacter sp. | — | GQ417497 | 1456/1463 (99.5%) |

Next, using the 16S rDNA nucleotide sequence of PEG8 strain, the top 20 strains shown in Table 2 and the 16S rDNA nucleotide sequence of *Enterobacter oryzae* Ola 51 strain, simplified molecular phylogenetic analysis was performed.

As the result of the simplified molecular phylogenetic analysis, the 16S rDNA nucleotide sequence of PEG8 strain was included in a cluster formed of the genus *Enterobacter* (FIG. 1). Furthermore, the 16S rDNA nucleotide sequence of PEG8 strain forms a cluster with the 16S rDNA nucleotide sequence of *Enterobacter oryzae* Ola 51 strain (FIG. 1). Note that, in FIG. 1, the numerical values attached to branches of the pylogenetic tree represent bootstrap values. On the other hand, 7 bases differ between the 16S rDNA nucleotide sequence of PEG8 strain and that of *Enterobacter oryzae* Ola 51 strain (data is not shown).

From the above results, it is considered that since PEG8 strain is close kin to *Enterobacter oryzae*; however, they have a clear difference between 16S rDNA nucleotide sequences, there is a high possibility that they are bacteria strains belonging to different species.

Example 3

[Analysis of Bacteriological Properties of PEG8 Strain]

PEG8 strain was subjected to morphology observation by an optical microscope (BX50F4, manufactured by Olympus Corporation) and to tests for a catalase reaction, an oxidase reaction, acid/gas production from glucose and oxidation/fermentation (O/F) of glucose based on the methods of Barrow et al. (Cowan and Steel's Manual for the Identification of Medical Bacteria. 3rd edition, 1993, Cambridge University Press). Furthermore, Gram-stainability was analyzed using Favor G "Nissui" (manufactured by Nissui Pharmaceutical Co., Ltd.). Moreover, PEG8 strain was tested for the items shown in Tables 4 and 5 by using API20E kit (manufactured by bioMérieux). Evaluation for each item was made in accordance with the manual attached to each kit.

TABLE 4

Bacteriological properties (morphology, etc.) of *Enterobacter* sp. PEG8 strain

| Item | Result |
|---|---|
| Cell morphology | Bacillus |
| Diameter of cell | 0.6-0.8 × 1.2-2.0 μm |
| Presence or absence of spores | − |
| Gram stainability | − |
| Mobility | + |
| Growth at 4° C. | − |
| Growth at 37° C. | + |
| Growth at 45° C. | + |
| Catalase reaction | + |
| Oxidase reaction | − |
| Acid/gas generation from glucose | +/+ |
| Oxidation/fermentation of glucose | +/+ |
| Growth in KCN medium | + |

Note that "+" represents being positive and "−" represents being negative.

TABLE 5

Bacteriological properties (assimilation, etc.) of *Enterobacter* sp. PEG8 strain

| Item | Result |
|---|---|
| β-galactosidase activity | + |
| Arginine dihydrolase activity | + |
| Lysine decarboxylase activity | − |
| Ornithine decarboxylase activity | − |
| Availability of citric acid | + |
| $H_2S$ production activity | − |
| Urease activity | − |
| Tryptophane deaminase activity | − |
| Indole production activity | − |
| Acetoin production activity | + |
| Gelatinase activity | − |
| Oxidase activity | − |
| $NO_2$ production activity | + |
| Reduction activity to $N_2$ | − |
| Growth in MacConkey agar medium | + |
| Glucose assimilation | + |
| D-mannitol assimilation | + |
| Inositol assimilation | − |
| D-sorbitol assimilation | + |
| L-rhamnose assimilation | + |
| White sugar assimilation | + |
| D-melibiose assimilation | − |
| D-amygdalin assimilation | + |
| L-arabinose assimilation | + |

Note that "+" represents being positive and "−" represents being negative.

PEG8 strain was cultured in LB agar medium at 30° C. for 48 hours and morphological observation was made. As a result, PEG8 strain formed opaque yellow colonies, having a diameter of 2.0-3.0 mm with the entire periphery fringe, being circular and having a smooth lenticular surface.

The analysis results of bacteriological properties of PEG8 strain were shown in Tables 4 and 5. The properties shown in Tables 4 and were analogous to those of *Enterobacter oryzae*; however, differences were also found (see Int. J. Syst. Evol. Microbiol., 2009, vol. 59, pages 1650-1655). PEG8 strain had neither lysine decarboxylase activity nor ornithine decarboxylase activity. In this respect, PEG8 strain differs from *Enterobacter oryzae*.

From the above results described in Examples 2 and 3, it is considered that since PEG8 strain is a close species to *Enterobacter oryzae* but has clear differences in 16S rDNA nucleotide sequence and bacteriological properties, PEG8 is a novel microorganism. Accordingly, PEG8 strain was concluded as a novel species of the genus *Enterobacter*. PEG8 strain has been deposited as *Enterobacter* sp. PEG8 at the Incorporated Administrative Agency National Institute of Technology and Evaluation Patent Microorganisms Depositary (NMPD) (2-5-8 Kazusakamatari, Kisarazu-shi, Chiba 292-0818, Japan) on Feb. 12, 2010 (Accession No. NITE BP-901).

Example 4

[Production of Hydrogen and 1,3-propanediol from Glycerol by Batch Culture]

The PEG8 strain, which was cultured in LB medium (5 ml) with shaking at 37° C. for 11 hours, was added to a 1 L mini-jar containing 500 ml of a raw-material liquid (composition; yeast extract: 2.5 g/L, peptone: 2.5 g/L, glycerol: 7 mass %, pH6.5). The gas of the mini jar was purged with nitrogen gas and culture was performed by using a 1 L-fermenter (BMJ-01PI, manufactured by ABLE & Biott) under an anaerobic condition at 37° C. and a shaking rate of 150 rpm. After culturing for 13 hours, about 50 ml of the culture solution was kept to remain and 450 ml of a fresh raw-material liquid was added and culturing was repeated. The culture solution and gas were serially sampled and hydrogen gas production, 1,3-propanediol production, ethanol production, residual glycerol amount and $OD_{660}$ value were measured.

1,3-propanediol, ethanol and glycerol were quantified by high-performance liquid chromatography in the following analysis conditions. Note that, a quantification method for measuring hydrogen gas is as described in Example 1.

Figure 2:
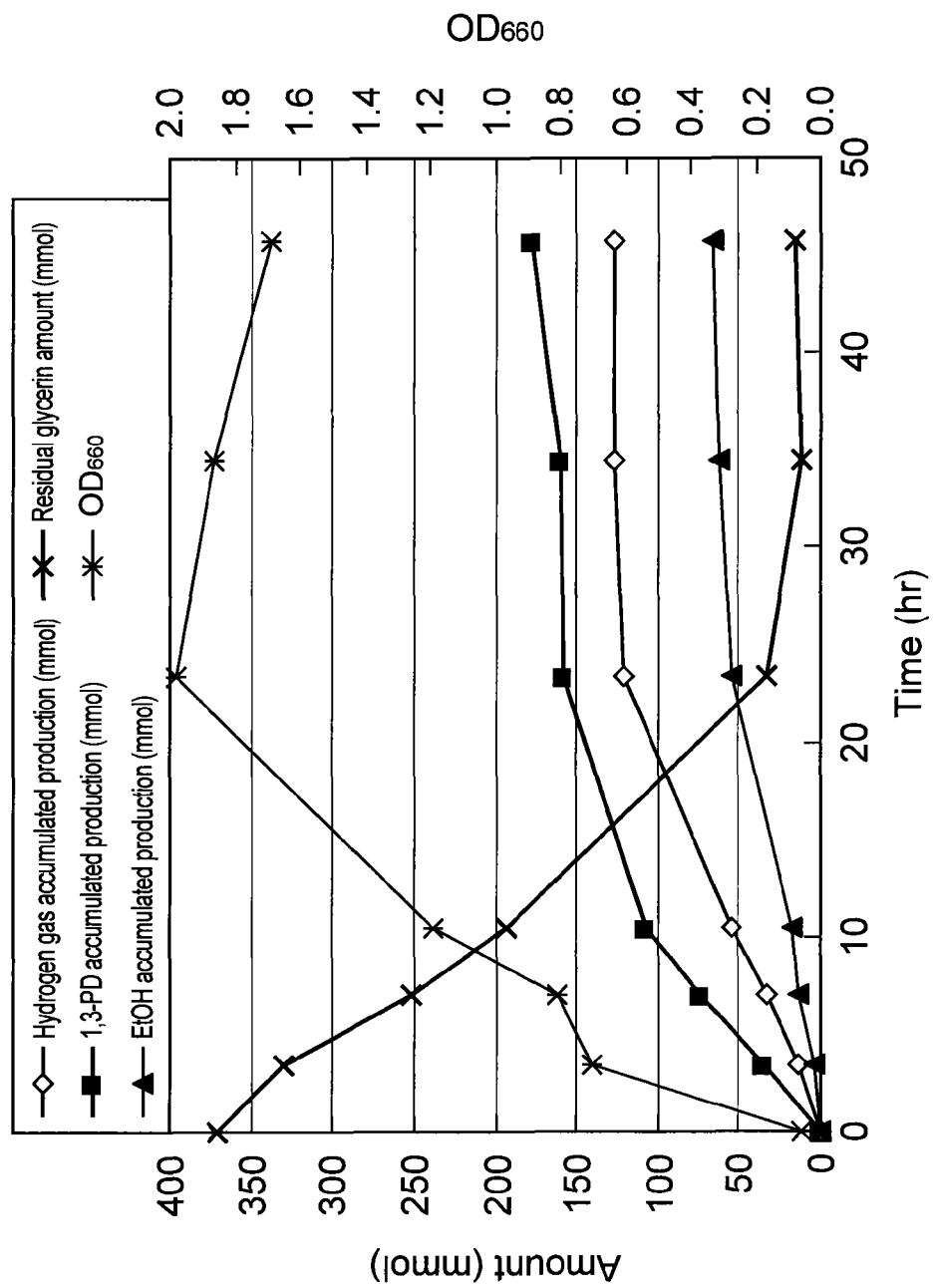
[FIG. 2] This is a graph showing a time-dependent change of hydrogen gas production, 1,3-propanediol production, ethanol production, residual glycerol amount and OD660 value when *Enterobacter* sp. PEG8 strain is subjected to batch culture.

Mobile liquid: pure water
Column: Shim-pack SCR-102H (manufactured by Shimadzu)
Column temperature: 70° C.
Flow rate: 0.6 ml/min
Detector: Differential refractometer The results were shown in FIG. 2. As the number ($OD_{660}$) of bacteria of PEG8 strain increased, the residual glycerol amount decreased. This demonstrates that glycerol was degraded by PEG8 strain (FIG. 2). Furthermore, as glycerol was degraded, hydrogen gas, 1,3-propanediol and ethanol were produced (FIG. 2).

Example 5

[Effect of Glycerol Concentration]

A raw-material liquids (10 ml) (pH6.5) containing yeast extract (2.5 g/L), peptone (2.5 g/L), 2-morpholinoethanesulfonic acid (MES) (53.3 g/L) and glycerol (1.0%, 2.5%, 5.0%, 7.5%, 10.0%, 15.0%, 20.0%, 25.0% or 30.0% by mass, respectively) was poured in a 20 ml vial. To this, PEG8 strain was seeded and stationary culture was performed at 37° C. for 22 hours. After culturing, hydrogen gas production and $OD_{660}$ value were measured to analyze the effect of glycerol concentration.

Figure 3:
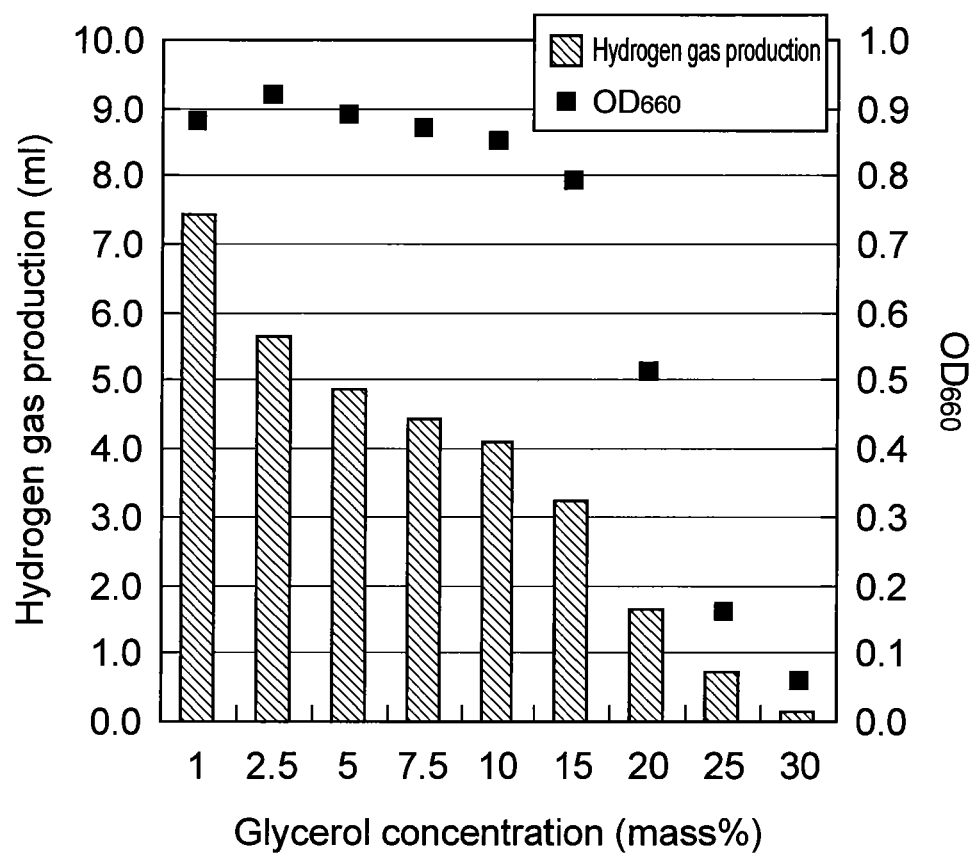
[FIG. 3] This is a graph showing hydrogen gas production when *Enterobacter* sp. PEG8 strain was cultured in different glycerol concentration conditions.

The results were shown in FIG. 3. PEG8 strain grew without any problem when glycerol is present in a concentration as high as 10 mass % and hydrogen gas production were maintained at a level corresponding to about 55% of the level at 1.0 mass % (FIG. 3). Furthermore, even at glycerol concentrations of 15.0 mass %, 20.0 mass %, 25.0 mass % and 30.0 mass %, hydrogen gas productions were maintained at levels corresponding to about 43%, about 22%, about 10% and about 2.2% of the level at 1.0 mass % (FIG. 3).

In *Enterobacter aerogenes* strain disclosed in Patent Literature 1, hydrogen gas is virtually not generated when a glycerol concentration exceeds 8 mass %. Therefore, the aforementioned tolerance to high glycerol concentration is a property which was not found in glycerol degradable bacteria conventionally used.

Example 6

[Change in Hydrogen Yield by Repetitive Batch Culture]

PEG8 strain was cultured in the same conditions as in Example 4 for 23 to 25 hours. After culturing, 50 ml of the culture solution was kept to remain and 450 ml of a fresh raw-material liquid was added and culturing was repeated. This procedure was repeated 8 times. Every after culturing, hydrogen production, 1,3-propanediol production and ethanol production were measured.

Figure 4:
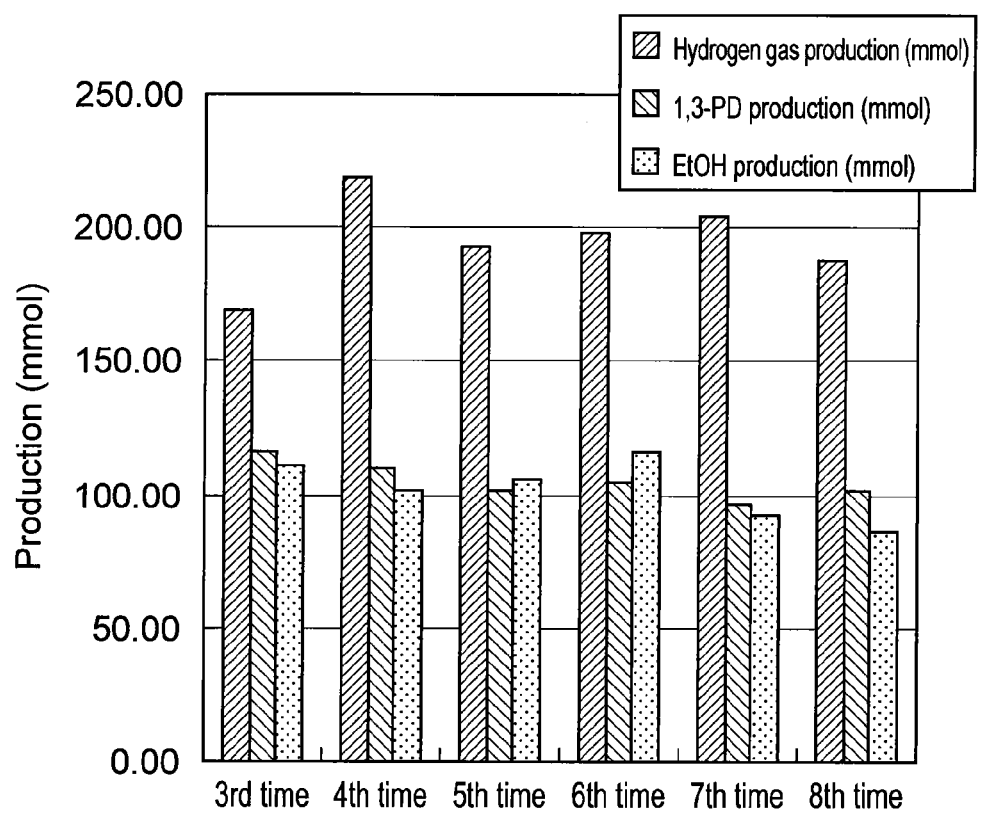
[FIG. 4] This is a graph showing hydrogen gas production, 1,3-propanediol production and ethanol production when *Enterobacter* sp. PEG8 strain was subjected to repetitive batch culture performed in raw-material liquid containing glycerol.

The results of the 3rd to 8th culturing time during which hydrogen is generated in a stable amount were shown in FIG. 4. In all culturing times, there were no significant changes in hydrogen production, 1,3-propanediol production and ethanol production (FIG. 4). More specifically, it was demonstrated that glycerol degradation, hydrogen production, 1,3- propanediol production and ethanol production can be stably performed by repetitive batch culture.

Example 7

[Change in Hydrogen Yield by Repetitive Batch Culture Using Biodiesel Liquid Waste]

PEG8 strain was cultured in the same conditions as in Example 4 for 23 to 25 hours except that biodiesel liquid waste (glycerol concentration: 87.6 mass %) was used in place of pure glycerol. After culturing, 50 ml of the culture solution was kept to remain and 450 ml of a fresh raw-material liquid was added and culturing was repeated. This procedure was repeated 8 times. Every after culturing, hydrogen production, 1,3-propanediol production and ethanol production were measured. Note that, as biodiesel liquid waste, liquid waste discharged when biodiesel was produced from vegetable oil as a raw material was used. Furthermore, the biodiesel liquid waste was added to a raw-material liquid such that the glycerol concentration corresponded to about 7.5 mass %.

Figure 5:
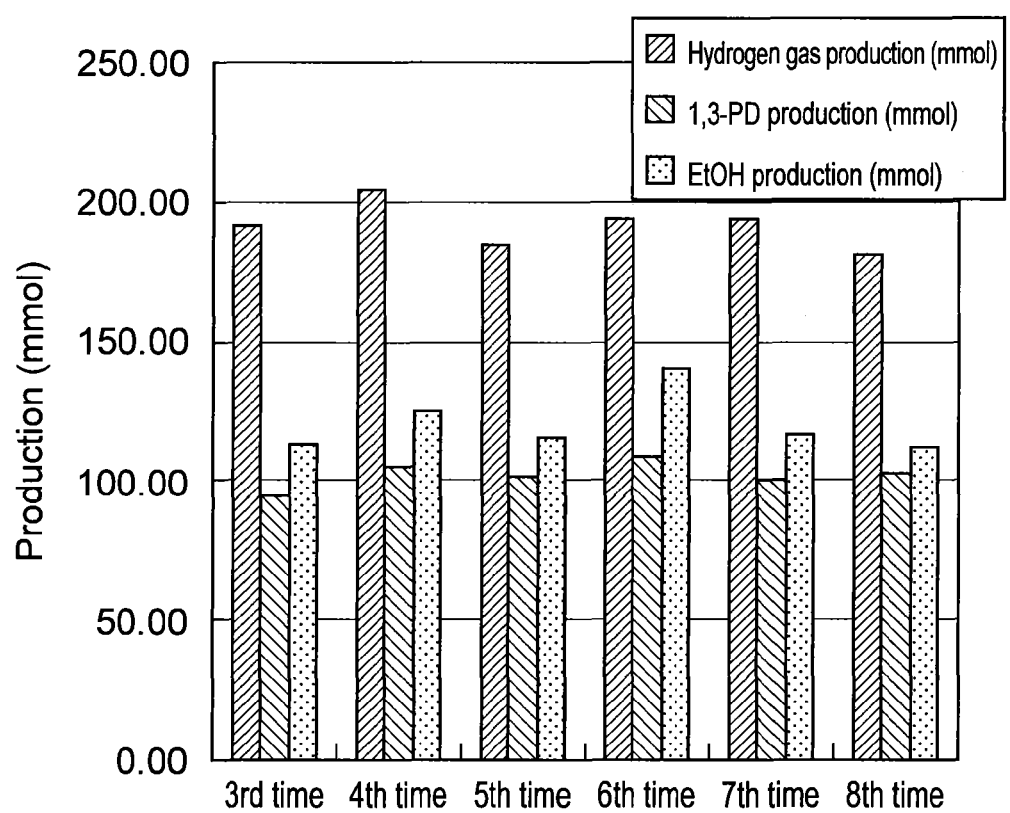
[FIG. 5] This is a graph showing hydrogen gas production, 1,3-propanediol production and ethanol production when *Enterobacter* sp. PEG8 strain was subjected to repetitive batch culture performed in raw-material liquid containing biodiesel liquid waste.

The results of the 3rd to 8th culturing time during which hydrogen is generated in a stable amount were shown in FIG. 5. In all culturing times, there were no significant changes in hydrogen production, 1,3-propanediol production and ethanol production (FIG. 5). More specifically, it was demonstrated that glycerol degradation, hydrogen production, 1,3-propanediol production and ethanol production can be stably performed by repetitive batch culture, even if biodiesel liquid waste was used.

Example 8

[Other Properties of PEG8 Strain]

To analyze properties of PEG8 strain, effect of medium pH, effect of fermentation temperature, effect of ethanol in a medium and assimilation of various types of carbon sources were tested.

Effect of medium pH was analyzed by pouring a raw-material liquid (10 ml) containing yeast extract (2.5 g/L), peptone (2.5 g/L), glycerol (1.0 mass %) and 0.4M Good buffer in 20 ml vial and seeding PEG8 strain, culturing it at 37° C. for 18 hours and measuring hydrogen gas production in the cases where pH was set within the range of 4.5 to 8.0. At pH of 5.0, 5.5, 6.0, 6.5 and 7.0, MES was used as Good buffer and 2-[4-(2-hydroxyethyl)-1-piperazinyl]ethane-sulfonic acid (HEPES) was used at pH of 7.5 and 8.0 as Good buffer. Furthermore, at pH of 4.5, Good buffer was not added.

The results were shown in Table 6. Acidic medium pH was advantageous for generating hydrogen gas.

TABLE 6

Effect of medium pH on hydrogen gas production

| pH | Hydrogen gas production (ml) | $OD_{660}$ |
| --- | --- | --- |
| 4.5 | 1.2 | 0.15 |
| 5.0 | 3.8 | 0.56 |
| 5.5 | 4.7 | 0.82 |
| 6.0 | 4.6 | 1.04 |
| 6.5 | 3.1 | 1.32 |
| 7.0 | 2.2 | 1.40 |
| 7.5 | 1.2 | 1.46 |
| 8.0 | 0.5 | 1.48 |

Effect of fermentation temperature was analyzed by pouring a raw-material liquid (10 ml) containing yeast extract (2.5 g/L), peptone (2.5 g/L), glycerol (1 mass %) and 250 mM MES (pH6.5) in 20 ml vial and seeding PEG8 strain, culturing it for 22 hours at temperatures of 15° C., 20° C., 25° C., 30° C., 34° C., 37° C. and 40° C., and measuring hydrogen gas production.

The results were shown in Table 7. Production of hydrogen gas was a maximum at a fermentation temperature of near 34° C., and decreased as the fermentation temperature increased and decreased from 34° C.

TABLE 7

Effect of fermentation temperature on hydrogen gas production

| Fermentation temperature (° C.) | Hydrogen gas production (ml) | $OD_{660}$ |
| --- | --- | --- |
| 15 | 0.6 | 0.25 |
| 20 | 1.5 | 0.58 |
| 25 | 2.7 | 0.71 |
| 30 | 3.4 | 0.72 |
| 34 | 5.9 | 0.71 |
| 37 | 4.6 | 0.65 |
| 40 | 3.1 | 0.44 |

Effect of ethanol in medium was analyzed by performing culture in a raw-material liquid containing yeast extract (2.5 g/L), peptone (2.5 g/L), glycerol (1 mass %), 250 mM MES (pH6.5) and ethanol at 37° C. for 17 hours and measuring hydrogen-gas production in the cases where ethanol concentration was set at 0, 1, 2 and 3 vol %.

The results were shown in Table 8. As the concentration of ethanol increased, hydrogen gas production decreased.

TABLE 8

Effect of ethanol in medium on hydrogen gas production

| Ethanol concentration (vol %) | Hydrogen gas production (ml) |
| --- | --- |
| 0 | 4.8 |
| 1 | 4.9 |
| 2 | 4.2 |
| 3 | 2.2 |
| 4 | 0 |

Assimilation tests of various types of carbon sources were each performed by adding the culture solution of PEG8 strain (0.5 ml) to a raw-material liquid (9.5 ml) pH6.5 containing yeast extract (2.5 g/L), peptone (2.5 g/L), MES (53.3 g/L), 1 mass % of a carbon source (glucose, maltose, maltotriose, dextrin, cellobiose, fructose, sucrose, xylose, arabinose or mannose), performing culture at 37° C. for 18 hours and measuring hydrogen gas production. Furthermore, after culturing, to the culture solution (0.5 ml), the raw-material liquid (9.5 ml) was added, and culture was performed at 37° C. for 18 hours and hydrogen gas production was measured. This procedure was repeated three times. Evaluation was performed based on the results of 4 cultures.

Figure 6:
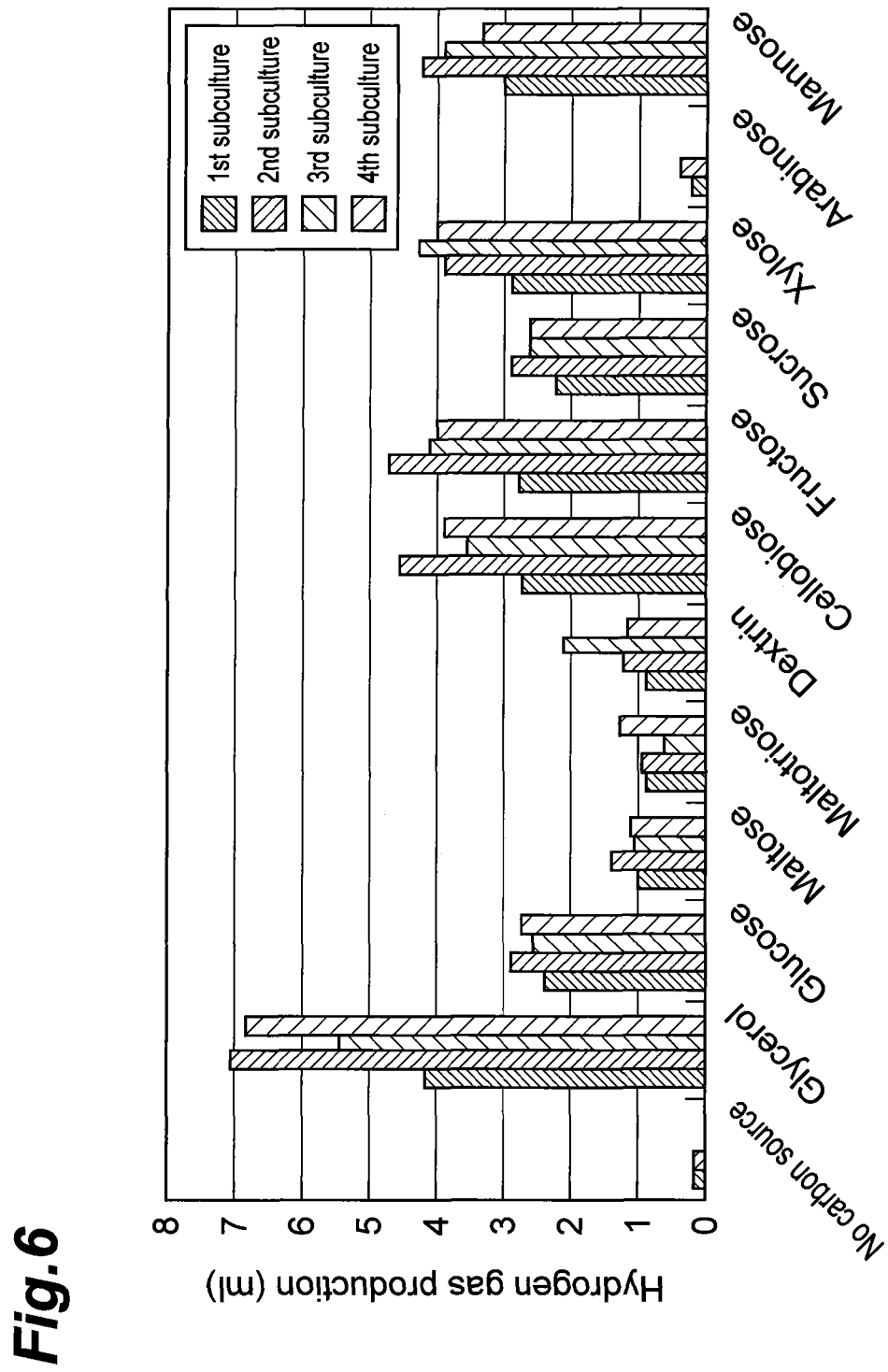
[FIG. 6] This is a graph showing hydrogen gas production, when *Enterobacter* sp. PEG8 strain was cultured in mediums containing different carbon sources.

The results were shown in FIG. 6. PEG8 strain assimilated not only glycerol but also other carbon sources except arabinose to produce hydrogen gas.

Example 9

[Other Properties 2 of PEG8 Strain]

Assimilation tests of various types of carbon sources (glucose, mannitol) were performed in the following conditions. To a raw-material liquid (9.5 ml) (pH6.5) containing yeast extract (2.5 g/L), peptone (2.5 g/L), MES 53.3 g/L and 2 mass % of each of carbon sources (glucose, mannitol) shown in FIG. 7, the culture solution of PEG8 strain (0.5 ml) was added. Culturing was performed at 34° C. for 19 hours and hydrogen gas production was measured. Furthermore, after culturing, to the culture solution (0.5 ml), the raw-material liquid (9.5 ml) was added. Culturing was performed at 34° C. for 19 hours and hydrogen gas production was measured. This procedure was repeated twice. Evaluation was performed based on the results of 3 cultures.

Figure 7:
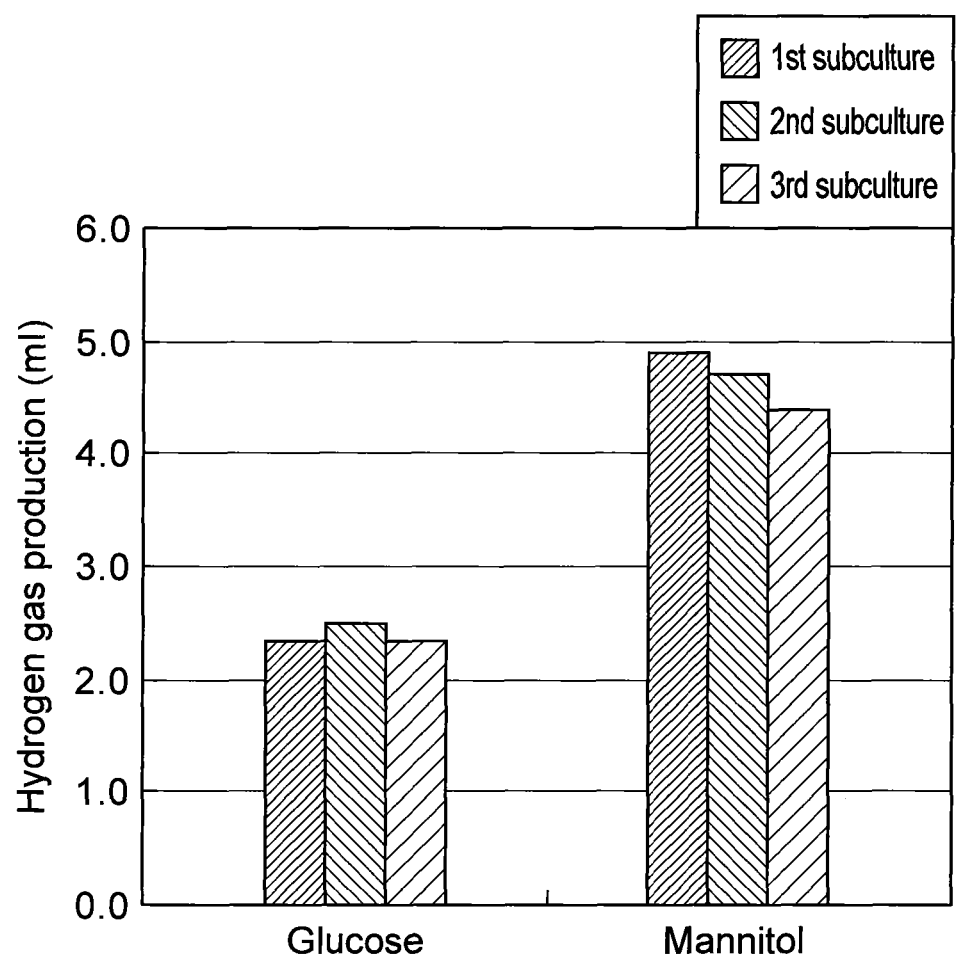
[FIG. 7] This is a graph showing hydrogen gas production, when *Enterobacter* sp. PEG8 strain was cultured in mediums containing different carbon sources.

The results were shown in FIG. 7. PEG8 strain assimilated not only glucose but also mannitol to produce hydrogen gas.

Industrial Applicability

The novel microorganism of the present invention can assimilate glycerol even in the presence of high-concentration glycerol and thus preferably be used for treating biodiesel liquid waste. Furthermore, the novel microorganism of the present invention can assimilate glycerol to produce hydrogen gas and 1,3-propanediol. These can be used as e.g., an energy source or resin materials. For example, hydrogen gas can be used as a fuel for fuel batteries, whereas 1,3-propanediol can be used as a raw material for one of synthetic fiber materials, i.e., polytrimethylene terephthalate (PTT).

The invention claimed is:

1. A process for producing hydrogen gas, the process comprising:
    contacting a raw material liquid comprising glycerol with the microorganism identified by Accession No. NITE BP-901 (*Enterobacter* sp. PEG8) at the Incorporated Administrative Agency National Institute of Technology and Evaluation Patent Microorganisms Depositary (NMPD) in a reaction vessel to produce hydrogen gas; and
    recovering the hydrogen gas from the reaction vessel by attaching a pipe or gas collection bag to said reaction vessel.

2. The process of claim 1, wherein the glycerol is contained in biodiesel liquid waste.

3. The process of claim 1, wherein said raw material liquid comprises biodiesel liquid waste with 0.1 to 35 mass % of glycerol.

4. A process for producing 1,3-propanediol, the processing comprising:
    contacting a raw material liquid comprising glycerol with the microorganism identified by Accession No. NITE BP-901 (*Enterobacter* sp. PEG8) at the Incorporated Administrative Agency National Institute of Technology and Evaluation Patent Microorganisms Depositary (NMPD) in a reaction vessel to produce 1,3-propanediol; and
    distilling the 1,3-propanediol by distillation apparatus.

5. The process of claim 4, wherein the glycerol is contained in biodiesel liquid waste.

6. The process of claim 4, wherein said raw material liquid comprises biodiesel liquid waste with 0.1 to 35 mass % of glycerol.

7. A method for treating biodiesel liquid waste, the method comprising:
    (a) degrading glycerol contained in biodiesel liquid waste with the microorganism identified by Accession No. NITE BP-901 (*Enterobacter* sp. PEG8) at the Incorporated Administrative Agency National Institute of Technology and Evaluation Patent Microorganisms Depositary (NMPD) in a reaction vessel to produce hydrogen gas and/or 1,3-propanediol; and
    (b) recovering the hydrogen gas from the reaction vessel by attaching a pipe or gas collection bag to said reaction vessel, or distilling the 1,3-propanediol by a distillation apparatus.

8. A method for treating biodiesel liquid waste, the method comprising:
    (a) contacting a raw-material liquid comprising biodiesel liquid waste comprising glycerol with the microorganism identified by Accession No. NITE BP-901 (*Enterobacter* sp. PEG8) at the Incorporated Administrative Agency National Institute of Technology and Evaluation Patent Microorganisms Depositary (NMPD) in a reaction vessel, to degrade the glycerol in the biodiesel liquid waste, to produce hydrogen gas and/or 1,3-propanediol, and decreasing glycerol up to a predetermined concentration;
    (b) recovering the hydrogen gas from the reaction vessel by attaching a pipe or gas collection bag to said reaction vessel, or distilling the 1,3-propanediol by a distillation apparatus; and
    (c) exchanging at least part of the raw-material liquid with decreased glycerol with a second raw-material liquid comprising biodiesel liquid waste.

* * * * *

SEQUENCE LISTING

<160> NUMBER OF SEQ ID NOS: 1

<210> SEQ ID NO 1
<211> LENGTH: 1500
<212> TYPE: DNA
<213> ORGANISM: Enterobacter sp.

<400> SEQUENCE: 1

```
gagtttgatc ctggctcaga ttgaacgctg gcggcaggcc taacacatgc aagtcgaacg      60
gtagcacaga gagcttgctc tcgggtgacg agtggcggac gggtgagtaa tgtctgggaa     120
actgcctgat ggaggggggat aactactgga aacggtagct aataccgcat aacgtcgcaa    180
gaccaaagag ggggaccttc gggcctcttg ccatcagatg tgcccagatg ggattagctg     240
gtaggygggg taatggccca cctaggcgac gatccctagc tggtctgaga ggatgaccag     300
ccacactgga actgagacac ggtccagact cctacgggag gcagcagtgg ggaatattgc     360
acaatgggcg caagcctgat gcagccatgc cgcgtgtgtg aagaaggcct tcgggttgta    420
aagcactttc agcggggagg aaggcggtac ggttaataac cgtgctgatt gacgttaccc    480
gcagaagaag caccggctaa ctccgtgcca gcagccgcgg taatacggag ggtgcaagcg    540
ttaatcggaa ttactgggcg taaagcgcac gcaggcggtc tgtcaagtcg gatgtgaaat    600
ccccgggctc aacctgggaa ctgcattcga aactggcagg ctggagtctc gtagagggag    660
gtagaattcc aggtgtagcg gtgaaatgcg tagagatctg gaggaatacc ggtggcgaag    720
gcggcctcct ggacgaagac tgacgctcag gtgcgaaagc gtgggagca aacaggatta     780 gataccctgg tagtccacgc cgtaaacgat gtcgatttgg aggttgtgcc cttgaggcgt    840
ggcttccgga gctaacgcgt taaatcgacc gcctgggag tacggccgca aggttaaaac     900
tcaaatgaat tgacggggc ccgcacaagc ggtggagcat gtggtttaat tcgatgcaac     960
gcgaagaacc ttacctggtc ttgacatcca cagarcctgg cagagatgcc ggggtgcctt   1020
cgggaactgt gagacaggtg ctgcatggct gtcgtcagct cgtgttgtga aatgttgggt  1080
taagtcccgc aacgagcgca acccttatcc tttgttgcca gcggtymggc cgggaactca   1140
aaggagactg ccagtgataa actggaggaa ggtggggatg acgtcaagtc atcatggccc   1200
ttacgaccag ggctacacac gtgctacaat ggcgcataca aagagaagcg acctcgcgag   1260
agcaagcgga cctcataaag tgcgtcgtag tccggattgg agtctgcaac tcgactccat   1320 gaagtcgaa tcgctagtaa tcgtgaatca gaatgtcacg gtgaatacgt tcccgggcct    1380
tgtacacacc gcccgtcaca ccatgggagt gggttgcaaa agaagtaggt agcttaacct   1440
tcgggagggc gcttaccact ttgtgattca tgactggggt gaagtcgtaa caaggtagcc   1500
```